(12) United States Patent
Kappel et al.

(10) Patent No.: US 8,870,817 B2
(45) Date of Patent: Oct. 28, 2014

(54) METHODS OF USING AN ADJUSTABLE VARIABLE STIFFNESS MEDICAL DEVICE

(71) Applicant: Boston Scientific Scimed, Inc., Maple Grove, MN (US)

(72) Inventors: Gary S. Kappel, Acton, MA (US); Jessica Schenck, Shrewsbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 14/091,601

(22) Filed: Nov. 27, 2013

(65) Prior Publication Data

US 2014/0088547 A1    Mar. 27, 2014

Related U.S. Application Data

(63) Continuation of application No. 13/590,790, filed on Aug. 21, 2012, now Pat. No. 8,622,957.

(60) Provisional application No. 61/526,359, filed on Aug. 23, 2011.

(51) Int. Cl.
| | | |
|---|---|---|
| *A61M 31/00* | (2006.01) | |
| *A61B 1/00* | (2006.01) | |
| *A61B 1/015* | (2006.01) | |
| *A61B 1/005* | (2006.01) | |
| *A61M 25/01* | (2006.01) | |
| *A61M 25/00* | (2006.01) | |

(52) U.S. Cl.
CPC .... *A61B 1/00078* (2013.01); *A61M 2025/0063* (2013.01); *A61B 1/015* (2013.01); *A61B 1/005* (2013.01); *A61M 25/0102* (2013.01); *A61B 1/00082* (2013.01); *A61M 25/0043* (2013.01)
USPC ........................................................ 604/103.09

(58) Field of Classification Search
USPC ........................................ 604/103.07, 103.09
See application file for complete search history.

(56) References Cited

U.S. PATENT DOCUMENTS

| | | | |
|---|---|---|---|
| 2,548,602 A | | 4/1951 | Greenburg |
| 3,774,596 A | | 11/1973 | Cook |
| 5,025,778 A | | 6/1991 | Silverstein et al. |
| 5,389,087 A | * | 2/1995 | Miraki ......................... 604/247 |
| 5,599,306 A | * | 2/1997 | Klein et al. .............. 604/103.01 |
| 5,634,902 A | * | 6/1997 | Johnson et al. ............ 604/96.01 |
| 5,947,940 A | | 9/1999 | Beisel |
| 6,632,235 B2 | * | 10/2003 | Weikel et al. ................. 606/192 |
| 6,893,417 B2 | * | 5/2005 | Gribbons et al. ......... 604/103.04 |
| 7,468,051 B2 | * | 12/2008 | Chan et al. ................. 604/96.01 |
| 7,670,333 B2 | * | 3/2010 | Schatzberger .................... 606/1 |
| 7,794,448 B2 | * | 9/2010 | Grandt et al. ................. 604/524 |
| 2004/0186378 A1 | | 9/2004 | Gesswein |
| 2005/0171445 A1 | * | 8/2005 | Millay et al. .................. 600/499 |
| 2005/0261707 A1 | * | 11/2005 | Schatzberger ................ 606/130 |
| 2010/0204537 A1 | * | 8/2010 | Hermann et al. ................. 600/7 |
| 2013/0053853 A1 | * | 2/2013 | Schmitz et al. ................. 606/83 |

* cited by examiner

*Primary Examiner* — Nicholas Lucchesi
*Assistant Examiner* — Diva K Chander
(74) *Attorney, Agent, or Firm* — Bookoff McAndrews, PLLC

(57) ABSTRACT

A transluminal device may include an elongate section extending between a proximal end and a distal end of the device. The elongate section may be configured to be inserted into a body cavity. The device may include a balloon within the elongate section between the proximal end and the distal end.

20 Claims, 4 Drawing Sheets

METHODS OF USING AN ADJUSTABLE VARIABLE STIFFNESS MEDICAL DEVICE

CROSS-REFERENCE TO RELATED APPLICATIONS

This application is a continuation of U.S. patent application Ser. No. 13/590,790, filed Aug. 21, 2012, which is based upon and claims the benefit of priority under 35 U.S.C. §119 (e) of U.S. Provisional Application No. 61/526,359 to Kappel et al. filed on Aug. 23, 2011, the entirety of both of which are incorporated herein by reference.

FIELD OF THE INVENTION

Embodiments of the present invention relate to a transluminal device with an adjustable variable stiffness flexible shaft. In particular, exemplary embodiments of the present invention relate to endoscopes, catheters and other transluminal devices that are inserted into a body. Embodiments of the present invention also cover methods of using such devices.

BACKGROUND OF THE INVENTION

A transluminal device is a flexible instrument introduced into the body for diagnostic or therapeutic purposes. These devices are inserted into the body through a natural or an artificially created opening, and are delivered to a work site inside the body through a body channel, such as, for example, the esophagus, a blood vessel, etc. Examples of transluminal devices include endoscopes, catheters, etc. Although the invention may be broadly applied to any transluminal device, for the sake of brevity and as an exemplary embodiment, the invention will be described as being applied to an endoscope in this disclosure.

Endoscopes are widely used for diagnostic and therapeutic purposes inside a body. There are many different uses for endoscopes, and typically, endoscope designs may be varied to optimize their performance for an intended application. For example, there are upper endoscopes for examination of the esophagus, stomach and duodenum, urethroscopes for examining the urethra and bladder, colonoscopes for examining the colon, angioscopes for examining the blood vessels and heart, bronchoscopes for examining the bronchi, laparoscopes for examining the peritoneal cavity, arthroscopes for examining joint spaces, etc. Each of these devices may include features to optimize their performance for the intended application.

In typical applications, a distal end of an endoscope is inserted into the body through a natural anatomic opening, such as, for example, the mouth, anus, vagina, etc. Endoscopes may also be inserted into the body through an incision created for the purpose. The distal end of the endoscope then proceeds from the point of insertion to a region of interest (work site) within the body by traversing a body channel. The endoscope may also include one or more lumens configured to deliver various diagnostic or treatment devices to the work site within the body. These diagnostic or treatment devices may include, among others, a light source, a viewing device, an irrigation lumen, an aspiration lumen, a temperature sensor, a heating probe, an ultrasonic sensor, a laser catheter or the like. These and other devices that may be used with an endoscope are broadly referred to as therapeutic or diagnostic tools in this application. Therapeutic tools configured for specific therapeutic tasks (such as, for example, incision, grasping, stitching, etc.) may also be delivered to the work site through the lumens of the endoscope.

To minimize patient discomfort, the diameter of an endoscope may be maintained at a size below the size of the body channel through which the endoscope passes. This size restriction may limit the number and size of the lumens in the endoscope. To minimize patient discomfort, endoscopes must also be sufficiently flexible to permit the distal end of the endoscope to follow the body cavity as the distal end progresses toward the work site. For example, as the endoscope traverses the hepatic flexure region of the digestive track, increased flexibility may be desirable. While greater endoscope flexibility may enable the endoscope to traverse tortuous body channels, it may be desirable to increase the stiffness of selected regions of the endoscope for improved maneuverability. For instance, when traversing the transverse colon region of the digestive track, increasing the stiffness of selected regions of the endoscope may be advantageous. Varying the stiffness of selected regions of the endoscope may also prevent kinking of the lumens passing therethrough.

SUMMARY OF THE INVENTION

An embodiment of the invention may include a transluminal device. The transluminal device may include an elongate section extending between a proximal end and a distal end of the device. The elongate section may be configured to be inserted into a body cavity. The device may include a balloon within the elongate section between the proximal end and the distal end.

Various embodiments of the invention may include one or more of the following aspects: a flexibility of the elongate section may be configured to decrease when the balloon is inflated, and the flexibility may be configured to increase when the balloon is deflated; the balloon may extend substantially from the proximal end to the distal end of the elongate section; a length of the balloon may be substantially smaller than a length of the elongate section; the balloon may include multiple independently inflatable segments; some segments of the multiple segments may be configured to inflate and deflate independently of other segments; the balloon may be fixed in the device; the device may include a lumen extending within the elongate section from the proximal end to the distal end, and the balloon may be positioned within the lumen and configured to be axially movable between the proximal end and the distal end; the device may be an endoscope; the balloon may have a semicircular cross-sectional shape.

Another embodiment of the invention may include a method of using a transluminal device. The method may include inserting a distal end of the device into a body cavity. The device may include a lumen extending from a proximal end of the device to the distal end. The method may also include positioning a balloon at a first location within the lumen, the first location being a location between the proximal end and the distal end, and moving the balloon from the first location to a second location in the lumen between the proximal end and the distal end. The method may also include inflating the balloon by admitting a fluid therein.

Various embodiments of the invention may include one or more of the following aspects: the method may further include inserting the balloon into the lumen; the step of inflating the balloon may be performed after positioning the balloon at the first location; the step of inflating the balloon may be performed before positioning the balloon at the first location; the method may further include deflating the balloon by removing the fluid therefrom; deflating the balloon may increase a flexibility of the device; inflating the balloon may include inflating a first section of the balloon independent of a second section of the balloon by admitting fluid into the first section while not admitting fluid into the second section, the first section and the second sections being different sections of the balloon; and inflating the balloon decreases a flexibility of the device.

Another embodiment of the invention may include a transluminal device. The device may include an elongate section extending between a proximal end and a distal end of the device. The elongate section may include a first region and a second region between the proximal end and the distal end. The device may also include a balloon. The balloon may be configured to increase a flexibility of the first region. The inflatable balloon may also be configured to increase the flexibility of the second region independently of increasing the flexibility of the first region.

Various embodiments of the invention may include one or more of the following aspects: the balloon may be configured to radially expand from a deflated configuration to an inflated configuration by admitting a fluid therein; the flexibility of the first region may be configured to increase from a first value corresponding to the deflated condition of the balloon to a second value corresponding to the inflated condition of the balloon; the device may also include a lumen extending within the elongate section from the proximal end to the distal end; the balloon may be disposed within the lumen; the balloon may be movable from the first region to the second region; the balloon may extend substantially from the proximal end to the distal end of the elongate section; a length of the balloon may be substantially smaller than a length of the elongate section; the balloon may include multiple segments that are configured to inflate and deflate separated by sections that do not substantially inflate and deflate when the fluid is admitted into or removed from the balloon; some segments of the multiple segments may be configured to inflate and deflate independently of other segments; the balloon may be fixed in the device; and the device may further include a wire configured to move the balloon between the first region and the second region.

BRIEF DESCRIPTION OF THE DRAWINGS

The accompanying drawings, which are incorporated in and constitute a part of this specification, illustrate embodiments of the invention and together with the description, serve to explain the principles of the invention.

DESCRIPTION OF THE EMBODIMENTS

Reference will now be made to exemplary embodiments of the invention, examples of which are illustrated in the accompanying drawings. Wherever possible, the same reference numbers will be used throughout the drawings to refer to the same or like parts.

Figure 1:
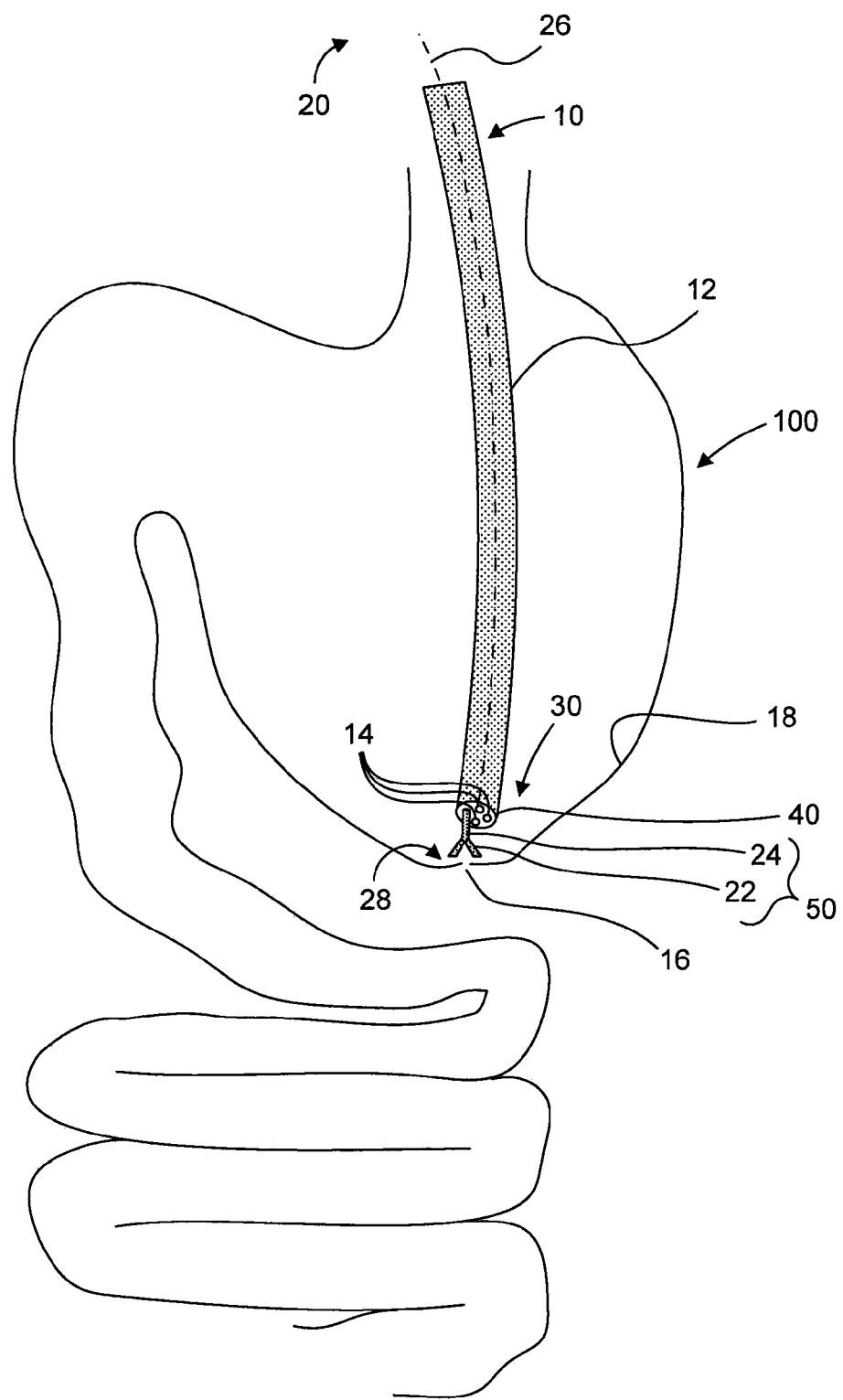
FIG. 1 is a schematic view of an embodiment of an endoscope with an adjustable variable stiffness flexible shaft performing an exemplary endoscopic surgery.

FIG. 1 depicts an exemplary endoscope 10 performing an exemplary endoscopic surgery. In the embodiment depicted in FIG. 1, the endoscope 10 may be inserted into the stomach 100 through the esophagus. The endoscope 10 may be positioned at a location proximate to a stomach wall 18 where a therapeutic procedure may be performed ("work site"). The work site 28 could include, for instance, a tear 16 on stomach wall 18. It should be emphasized that the illustrated application of the endoscope 10 in FIG. 1 is exemplary only, and that the endoscopes of the current disclosure may be applied to any endoscopic application known in the art.

The endoscope 10 may include a flexible elongate member 12 extending between a proximal end 20 and a distal end 30. In the configuration depicted in FIG. 1, the proximal end 20 may include the end of the endoscope 10 external to the body and the distal end 30 may include the end of the endoscope 10 internal to the body. Proximal end 20 may include actuation devices or other control mechanisms (not shown) that may be used to operate endoscope 10. For instance, these control mechanisms may allow an operator to move (translate, rotate, etc.) distal end 30 of endoscope 10 to position the distal end 30 in a preferred orientation to perform a desired therapeutic task. The flexibility of elongate member 12 may enable endoscope 10 to bend and pass through tortuous body passages as distal end 30 advances to work site 28. The endoscope 10 may be constructed of a plurality of materials some or all of which may be biocompatible. Typically, a part of the endoscope 10 that contacts the internal surfaces of a body may be made substantially of a biocompatible material.

The endoscope 10 may include a plurality of lumens 14 running longitudinally therethrough. Each lumen 14 may extend between the proximal end 20 external to the body and the distal end 30 internal to the body. In some embodiments, a longitudinal axis of the lumens may be substantially parallel to a longitudinal axis 26 of the endoscope 10. In some embodiments, lumens 14 may be formed integrally with endoscope 10, while in other embodiments lumens 14 may resemble small hollow tubes (or catheters) through a longitudinal cavity of endoscope 10. The lumens 14 may have any size and shape. In some embodiments, different lumens included in endoscope 10 may have different sizes and/or shapes. In some embodiments, some of lumens 14 may be dedicated for a particular task while other lumens may be hollow cavities, or working lumens, through which a desired therapeutic or diagnostic tool 50 may be delivered to work site 28. Some of lumens 14 dedicated for a particular task may include an irrigation lumen, an aspiration lumen, an illumination lumen, and a viewing lumen.

The irrigation lumen may be configured to deliver a fluid (such as, for example, a cleaning fluid) to work site 28. Irrigation lumen, therefore, may be configured to facilitate fluid flow therethrough. In some embodiments, proximal end 20 of the irrigation lumen may be configured to be attached to a source of fluid. In some embodiments, distal end 30 of the irrigation lumen may have devices (such as nozzles) configured to alter the flow of fluid exiting the lumen.

The aspiration lumen may be configured to remove fluid from work site 28. Aspiration lumen may, therefore, be configured to facilitate suction and/or fluid flow. In some embodiments, the flow of fluid through the aspiration lumen and the irrigation lumen may be in substantially opposite directions. For example, fluid may flow through an irrigation lumen towards the distal end 30, while fluid flow through the aspiration lumen may be towards the proximal end 20. Fluid flow through an irrigation lumen and an aspiration lumen may be independently operated, or their operation may be coordinated to perform a function, such as the extraction of a tissue sample from work site 28. In these embodiments, fluid may be delivered to work site 28 through the irrigation lumen, and a tissue sample may be removed from work site 28 through the aspiration lumen along with the fluid. The proximal end 20 of the aspiration channel may also be configured to be attached to a source of suction and/or a container configured, for example, to collect the tissue samples.

The viewing lumen may include devices configured to display a visual image of work site 28 external to the body. These devices may include imaging means (such as lens for a CCD, CMOS, or other camera) at distal end 30 and cables (electrical and/or optical cables) configured to transmit a recorded image to a display device external to the body. The illumination lumen may include devices configured to illuminate work site 28. These devices may include illumination devices (such as bulbs and/or other solid state light emitting devices) at distal end 30 and cables (such as fiber optic cables and/or light guides) configured to deliver power and other signals (such as, instructions) to these illumination devices. In some embodiments, viewing and illumination lumens may include a lens and/or other devices that facilitate illumination and viewing of work site 28.

The working lumens may include a hollow cavity that extend from proximal end 20 to distal end 30 of endoscope 10. These lumens 14 may be configured to deliver a therapeutic tool or diagnostic 50 to work site 28. A distal end of the therapeutic tool 50 may be inserted into a lumen 14 and pushed down the length of elongate section 12 to extend an end effector 22 at work site 28. One or more therapeutic or diagnostic tools 50 may be delivered to work site 28 through lumen 14.

Some or all of these lumens 14 may have a substantially circular cross-section. However, it is also contemplated that they may have any suitable shape, size, and/or configuration. For instance, in some embodiments, the shape of the lumen 14 may be specially tailored to pass an end effector 22 without a corresponding increase in diameter of endoscope 10.

Therapeutic tool 50 may include a shaft 24 that connects the end effector 22 to an actuation device (not shown) external to the body. The actuation device may be configured to operate the end effector 22. Operation of the end effector 22 may include performing a desired therapeutic task at work site 28. The end effector 22 may include any medical instrument configured to perform the desired therapeutic task at the work site 28. Non-limiting examples of end effectors 32 may include biopsy forceps, baskets, graspers, snares, surgical knives, needles, suturing instruments, heating elements for cauterizing instruments, a laser lithotripter, etc. In some embodiments, the actuation device may also be configured to move (that is, translate, rotate, etc.) the end effector 22 at work site 28. The actuation device may be attached to proximal end 20 of endoscope 10 and may be part of a larger control mechanism or it may be a separate control mechanism.

Figure 2:
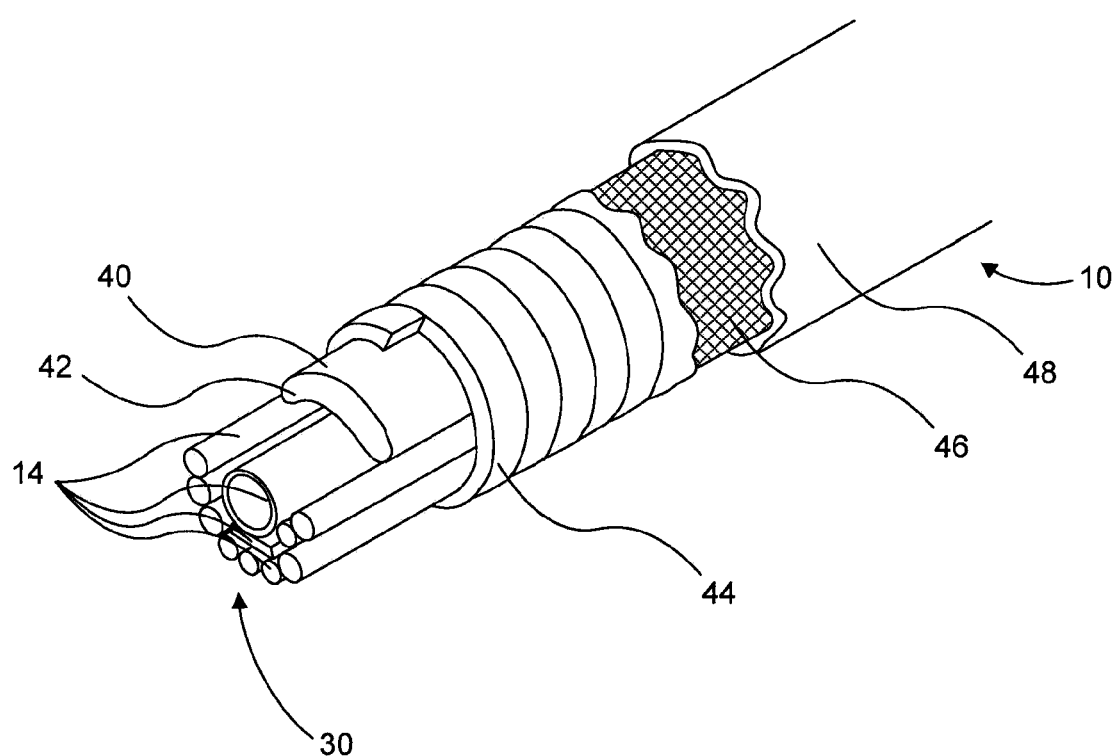
FIG. 2 is an illustration of the distal end of the endoscope of FIG. 1.

Endoscope 10 may also include an inflatable balloon 40 passing therethrough. Inflatable balloon 40 may be any device that may radially expand (inflate) when filled with a fluid, and radially contract when the fluid is removed. In addition to radial expansion, inflation of some embodiments of inflatable balloon 40 may also include longitudinal expansion. FIG. 2 shows an illustration of an embodiment of distal end 30 of endoscope 10. It should be emphasized that the structure of the endoscope illustrated in FIG. 2 is exemplary only, and in general, the inventive concepts of the current application may be applied to any endoscope known in the art. In the illustration of FIG. 2, some external parts of endoscope 10 have been removed to illustrate parts within. As described earlier, multiple lumens 14 may extend from proximal end 20 of endoscope 10 to distal end 30. Some of these lumens 14 may be dedicated for a particular task while other lumens may be hollow cavities, or working lumens, through which a desired therapeutic tool 50 may be delivered to work site 28.

An inflatable balloon 40 may also extend to distal end 30 alongside lumens 14. Although inflatable balloon 40 is depicted as a relatively large semicircular segment in the embodiment illustrated in FIG. 2, inflatable balloon 40 may possess any shape and size. In some embodiments, the shape and size of inflatable balloon 40 may be tailored to optimize the use of available space within endoscope 10.

In some embodiments, balloon 40 may include a taper at one or both of its proximal and distal ends. The tapered end of the balloon 40 may help in moving the balloon through the lumen. In some embodiments, balloon 40 may include reinforcing features such as webbing in the walls or the surface to increase a stiffness and/or the strength of the balloon 40 in selected regions. In some embodiments, balloon 40 may include internal stylets, support catheters or the like to assist in advancing the balloon 40 through a lumen. In some embodiments, the wall thickness of the material may be selected based on a desired strength or rigidity of the balloon 40. In some embodiments, balloon 40 may include filament loops or other connectors to assist in retracting the balloon 40 or to move the balloon 40 from one location to another.

In some embodiments, inflatable balloon 40 may extend through a lumen 14 of endoscope 10 while in other embodiments, inflatable balloon 40 may be embedded in endoscope 10. In embedded embodiments, inflatable balloon 40 may be built-in anywhere in endoscope 10. In embodiments where inflatable balloon 40 extends through lumen 14, inflatable balloon 40 may extend through any lumen 14 of endoscope 10. The balloon 40 may also have a shape to match the shape of the lumen. In these embodiments, inflatable balloon 40 may be an accessory that an operator may insert into lumen 14 and inflate as desired. Inflatable balloon 40 may also be pre-fixed in a lumen. In such an embodiment, an operator may insert a lumen with an inflatable balloon 40 pre-attached to it, into endoscope 10. Inflatable balloon 40 may include an expandable sheath 42 enclosing a cavity. Sheath 42 may be constructed from any biocompatible material, including elastomeric, rubber, or other materials which permits inflatable balloon 40 to be radially flexible. Non-limiting examples of balloon 40 materials may include materials such as polyethylene terephthalate (PET) and Nylon. Inflatable balloon 40 may be configured to inflate and deflate as desired to selectively vary the flexibility of endoscope 10. In some embodiments, the sheath 42 of balloon 40 may have a low compliance to support the endoscope without overexpansion. In general, the balloon 40 may have any cross-sectional shape and length. For example, in some embodiments, balloon 40 may have a cross-sectional shape that is circular, semi-circular, oval, elliptical, or another curved shape. In some embodiments, the cross-sectional shape of balloon 40 may resemble the segment of a circle. It is also contemplated that, in some embodiments, the shape of balloon 40 may resemble an annular ring or a segment of an annular ring.

Inflation of inflatable balloon 40 may be accomplished by filling the sheath 42 with a fluid. Any fluid, such as air, water or a liquid, may be used to fill inflatable balloon 40. Deflating inflatable balloon 40 may be accomplished by draining the fluid from sheath 42. In the deflated configuration, endoscope 10 may be highly flexible. That is, elongate member 12 of endoscope 10 may flex or bend relatively easily. This flexibility of elongate member 12 may assist endoscope 10 to navigate around curved or winding body cavities as it advances towards work site 28. In the inflated configuration, the flexural rigidity ("rigidity") of the portion of endoscope 10 that include inflatable balloon 40 increases. That is, the flexibility of elongate member 12 decreases. Controlling the amount of fluid in inflatable balloon 40 may vary the flexibility of endoscope 10 between low flexibility (that is, high rigidity) in a fully inflated configuration to high flexibility (that is, low rigidity) in a fully deflated configuration.

Inflatable balloon 40 may be fluidly coupled to a fluid (air, water, liquid, etc.) source at proximal end 20 of endoscope 10. The fluid source may include any reservoir of the fluid such as, for example, a tank of air, a needle or other reservoir of fluid, etc. Proximal end of endoscope 10 may also include a control mechanism (or other activation means) that may be used to inflate and deflate inflatable balloon 40. The control mechanism may include, but not limited to, pumps (manual, electric, etc.), storage reservoirs (tanks, etc.), valves (mechanical, electric, electronic, etc.), computer controls, etc. In some embodiments, the control mechanism may include programmable logic that enables the inflatable balloon 40 to be inflated to suit a particular region of the body. The control mechanism may be included along with other controls of endoscope 10, or it may be a stand alone control mechanism. In one embodiment, the control mechanism may be operated to pump fluid from the fluid source to inflatable balloon 40 to increase the rigidity of endoscope 10. The control mechanism may also be operated to drain fluid from inflatable balloon 40 to deflate inflatable balloon 40, and thereby, increase the flexibility of endoscope 10.

Inflatable balloon 40 may provide the ability to control the flexibility of endoscope 10 during a therapeutic procedure. In some instances it may be desirable to change the flexibility of an endoscope during a procedure. For example, as endoscope 10 is inserted into the human body, a sufficiently stiff distal end 30 may permit endoscope 10 to be pushed into the body cavity. During insertion, a stiff distal end 30 may prevent endoscope 10 from bending on itself or kinking when being pushed into a tight body cavity or lumen. When distal end 30 traverses through a bend in body cavity to reach work site 28, it may be desirable to sufficiently decrease the stiffness of endoscope 10 to allow distal end 30 to navigate the bend without damaging body tissue. Once distal end 30 reaches work site 28, for some therapeutic tasks, it may be desirable to make the distal end 30 more rigid or more flexible to perform the medical procedure.

Endoscope 10, which encloses lumens 14 and inflatable balloon 40, may be constructed by any means known in the art. In some embodiments, multiple lumens 14 and inflatable balloon 40 may be enclosed by a winding 44. Winding 44 may be made of any material, such as a metal, an elastomeric, a plastic, a fabric, or a rubber material. Winding 44 may have the form of a thin strip of material wrapped around lumens 14 and inflatable balloon 40. This structure of the winding 44 may enable endoscope 10 to be flexible. Winding 44 may be covered by an inner cover 46 and an outer cover 46. Inner cover 46 and/or outer cover 48 may comprise water proof material that prevents biological fluids from seeping into endoscope 10. Inner cover 46 and/or outer cover 48 may also be made of flexible biocompatible materials. The external surface of outer cover 48 may be sufficiently lubricious so that endoscope 10 may traverse body cavities without patient discomfort. Although FIG. 2 illustrates an embodiment of endoscope 10 with winding 44 wrapped by inner cover 46 and outer cover 48, it should be emphasized that this illustration is exemplary only, and endoscope 10 may have any structure known in the art. For instance, in some embodiments, endoscope 10 may only include a cover which encloses lumens 14. In some embodiments, it may be desirable to reduce the radial expansion of endoscope 10 as inflatable balloon 40 is inflated. In these embodiments, the number and/or the material of these covers may be chosen to prevent the radial expansion of endoscope 10.

Figures 3A, 3B:
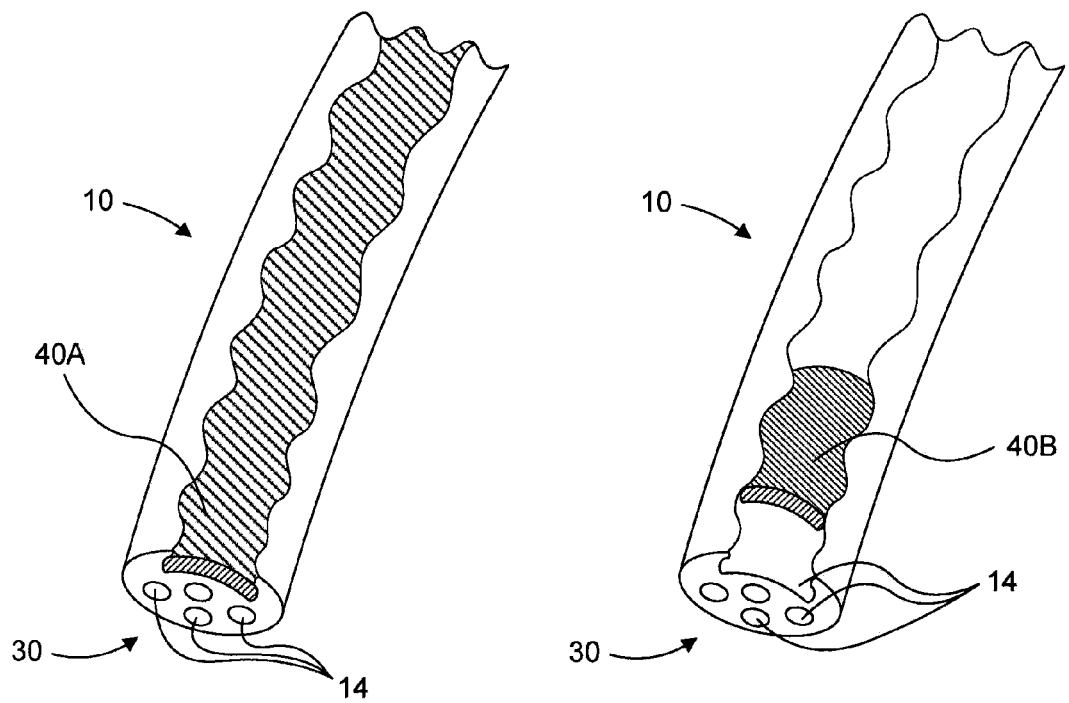
FIG. 3A-3C are illustrations of three different embodiments of the inflatable balloon of the endoscope of FIG. 1.
Figure 3C:
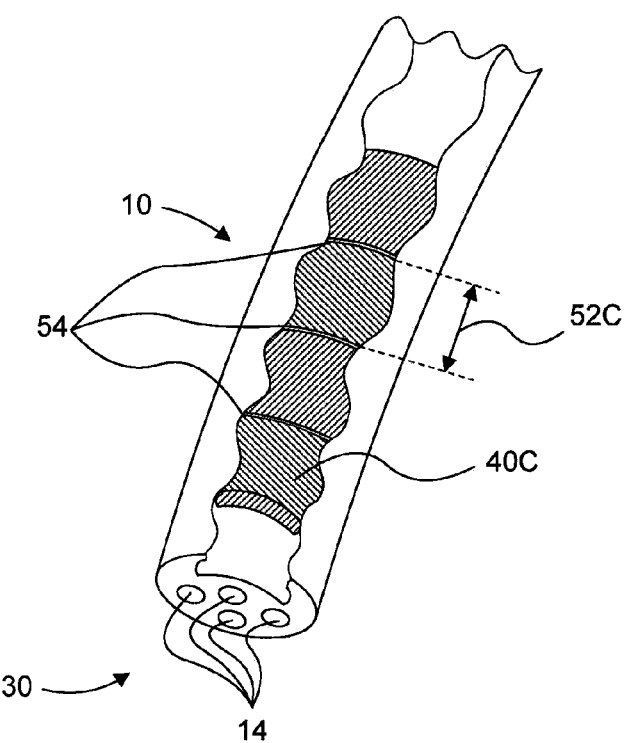

Balloon 40 may have any length. In some embodiments, the length of the balloon 40 may be selected to match the length of a body tract. For instance, in some embodiments, the length of balloon 40 may approximately match a length of flexible section of a body tract. In some embodiments, balloon 40 may be a continuous length balloon that extends substantially the entire length (from proximal end 20 to distal end 30) of endoscope 10. In other embodiments, balloon 40 may have a length smaller than the length of endoscope 10. FIGS. 3A-3C illustrate three embodiments of inflatable balloons that may be used with endoscope 10. In the embodiment of FIG. 3A, inflatable balloon 40A extends substantially the entire length of endoscope 10. In such an embodiment, inflation of inflatable balloon may increase the rigidity of the entire length of endoscope 10. Such an embodiment of inflatable balloon 40A may be desirable for some therapeutic procedures where increasing the stiffness of the entire endoscope may make the procedure easier.

Inflatable balloon 40A may be embedded or fixed in endoscope 10 or it may extend through a lumen 14. In an embodiment where inflatable balloon 40A may be embedded, it may be built-in anywhere on endoscope, such as, for example, between winding 44 and inner cover 46 of FIG. 2. In an embodiment where inflatable balloon 40A extends through a lumen 14, inflatable balloon 40A may be removed and inserted into lumen 14 as desired. For embodiments where inflatable balloon 40 is a continuous length balloon, selectively reducing the stiffness of a region of endoscope 10 may include removing the inflatable balloon 40 from that section of endoscope 10. Removing inflatable balloon 40 from a section of endoscope 10 may include pulling (or pushing) inflatable balloon 40 away from that section of endoscope 10. For instance, to reduce the stiffness of distal end 30 of endoscope 10, inflatable balloon 40 may be removed from the distal end 30 by pulling a section of inflatable balloon 40 out of lumen 14 from proximal end 20.

FIG. 3B illustrates an embodiment where the length of inflatable balloon 40B may be smaller than the length of endoscope 10. In such an embodiment, the location of inflatable balloon 40B along the length of endoscope 10 may be fixed or it may be movable along the length of endoscope 10. In embodiments where the location of inflatable balloon 40B may be fixed, inflatable balloon 40 may be fixed at a location where it may be desirable to vary endoscope flexibility. In such an embodiment inflatable balloon 40B may be embedded in endoscope 10 or it may be fixed within lumen 14. In an embodiment where the location of inflatable balloon 40B may be varied, inflatable balloon 40B may travel within lumen 14. In such an embodiment, wires, links or other mechanisms attached to inflatable balloon 40B may extend to proximal end 20 of endoscope 10. Pulling or pushing these wires or links may move inflatable balloon 40B along the length of lumen 14. These wires, links, or other mechanisms may allow inflatable balloon 40B to be pulled into position at a location where a change in endoscope flexibility is desired. Inflatable balloon 40B may have any length up to the length of endoscope 10. In some embodiments, inflatable balloon 40B may be small and extend only a small length of endoscope 10, while in other embodiments inflatable balloon 40B may be longer.

Inflatable balloon 40B may be used for therapeutic or diagnostic procedures where it may be desirable to vary the stiffness of selected lengths of endoscope 10. For instance, in a colonoscopic procedure, when the tip of the endoscope is advanced halfway up the cecum, it may be helpful for the portion of the endoscope at the anal verge to be relatively rigid and inflexible, while the portion beyond the anal verge may need to be relatively flexible. In such an application, selected regions of the endoscope may be made flexible or rigid by positioning and inflating inflatable balloon 40B at the desired location, as the endoscope is advanced through the colon.

FIG. 3C illustrates another embodiment of inflatable balloon which may be used to vary the flexibility of endoscope 10. In the embodiment of FIG. 3C, inflatable balloon 40C may include a series of segmented balloons extending from proximal end 20 to distal end 30. Inflatable balloon 40C of this embodiment may include multiple balloon segments of length 52C separated by a non-inflatable section 54. The length of each segment may be the same or it may be different. In an inflated configuration, the non-inflatable sections 54 may be regions of reduced stiffness that may allow endoscope 10 to flex about these regions. In some embodiments of inflatable balloon 40C, the balloon may extend substantially the entire length of endoscope 10. In other embodiments, inflatable balloon 40C may have a smaller length. In some embodiments, ducts or access ports passing through non-inflatable sections may connect individual balloon segments so that fluid may pass between these segments. In other embodiments, individual balloon segments of the inflatable balloon 40C may be inflated individually. In such an embodiment, selected balloon segments may be inflated and selected balloon segments deflated to vary the stiffness of different regions of endoscope 10.

Inflatable balloon 40C may be embedded in endoscope 10 or it may be pulled to a desired position as in the embodiment of FIG. 3B. In such an embodiment, as in the embodiment of FIG. 3B, links or other mechanisms attached to inflatable balloon 40C may allow inflatable balloon 40C to be pulled into position at a location where a change in endoscope flexibility is desired. Other embodiments of inflatable balloon may include a combination of continuous sections and segments which may be pulled into a desired location as needed.

Figure 4:
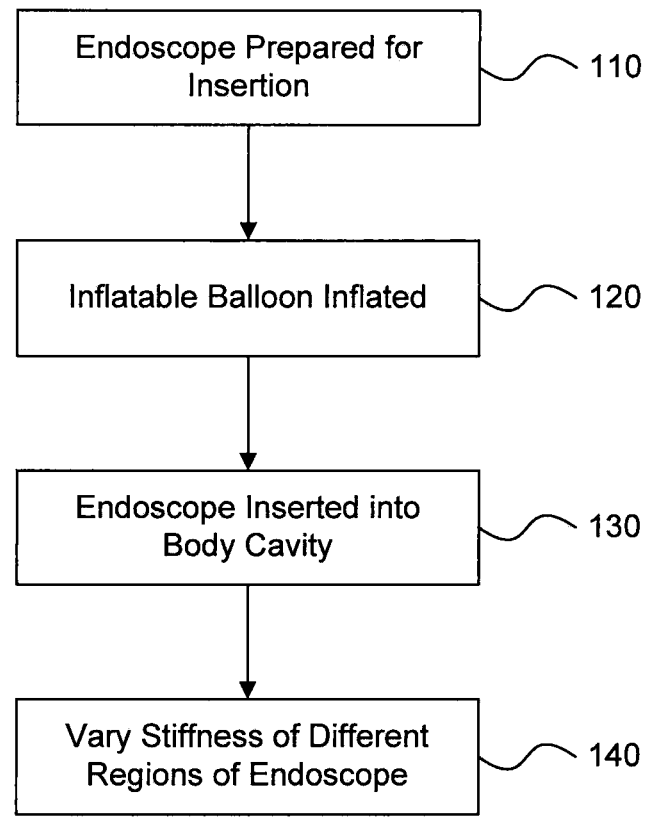
FIG. 4 is an illustration of a method of using an embodiment of the current invention.

FIG. 4 illustrates a method of using endoscope 10 with an adjustable variable stiffness flexible shaft. Endoscope 10 first may be prepared to be inserted into a body cavity (step 110). In some embodiments, this step may include cleaning the endoscope and/or inserting desired devices (such as, for example, illumination and viewing devices) into lumens 14 of endoscope 10. In some embodiments, this step may include inserting an inflatable balloon 40 into a lumen 14 of endoscope 10 and fluidly coupling inflatable balloon 40 to a fluid reservoir. As indicated earlier, in some embodiments, inserting an inflatable balloon into lumen 14 of endoscope 10 may include inserting a lumen with a pre-attached inflatable balloon into endoscope 10. In some embodiments, the inflatable balloon 40 may also be coupled to a link of sufficient length that will extend out of the proximal end of lumen 14 when inflatable balloon 40 is inserted into the lumen. In an embodiment where inflatable balloon 40 is embedded in the endoscope, step 110 may include coupling inflatable balloon 40 to the fluid reservoir.

The inflatable balloon 40 at the distal end of endoscope 10 may be inflated in step 120. In some embodiments, this step may also include positioning inflatable balloon 40 at a desired location (such as, for instance at the distal end 30 of endoscope 10). Positioning inflatable balloon 40 at a desired location may be accomplished by pushing/pulling a link coupled to inflatable balloon 40. In some embodiments, a lumen with an inflatable balloon 40 disposed within it is pulled/pushed to position inflatable balloon 40 at a desired location. Inflatable balloon 40 may be positioned at a desired location before or after it is inflated. That is, inflatable balloon 40 may be positioned at a desired location before being inflated, or the inflatable balloon 40 may be inflated first before being positioned a desired location. Inflating inflatable balloon 40 at a desired location may increase the stiffness of that location of endoscope 10. In some applications, inflatable balloon 40 may be inflated at distal end 30 of endoscope 10 to selectively increase the stiffness of the distal end.

The distal end 30 of the endoscope 10 may be inserted into a body cavity through an anatomic opening in step 130. The increased stiffness of the distal end of endoscope 10 may assist insertion of endoscope 10 into the body cavity. For example, in an application of inflatable balloon 40 to a colonoscope (a type of endoscope used for therapeutic procedures on the colon), increased rigidity of the distal end may allow the colonoscope to be inserted into the anal cavity through the anus. The increased rigidity of the distal end may also allow the colonoscope to advance through a constricted anal cavity without compressing or kinking. In some embodiments, the endoscope may be inserted in to the body cavity (step 130) before the inflatable balloon is inflated (step 120).

As distal end 30 of endoscope 10 advances through the body cavity, it may be desirable to reduce the stiffness of distal end 30 to reduce the possibility of trauma to body tissue. The stiffness of distal end 30 may be reduced by deflating the inflatable balloon slightly. In some embodiments, an operator may deflate and inflate inflatable balloon 40 multiple times to obtain a desired stiffness of the endoscope distal end 30. The desired stiffness of distal end 30 may be based on experience of the operator and may be a level of inflation that allows endoscope 10 to advance along the body cavity easily without causing undue trauma to the patient.

Once distal end 30 advances into a region of the body cavity which is not constricted, it may be desirable to reduce the rigidity of the region of endoscope 10 in the unconstricted body cavity further, while maintaining the stiffness of the region of endoscope 10 in the constricted body cavity (step 140). For example, in the application of the colonoscope advancing through the anal canal described earlier, once the colonoscope is past the anal verge (distal end of the anal canal), it may be desirable to keep the region of the colonoscope past the anal verge relatively flexible while maintaining the region of the colonoscope in the anal canal relatively rigid and inflexible. In some embodiments, it may be desirable to increase the stiffness of one region of endoscope while decreasing the stiffness of another region. In some embodiments, it may be desirable to deflate the endoscope shaft to make the shaft soft and/or flexible for easy and non-traumatic removal of the endoscope from the body cavity. In other embodiments it may be desirable to increase the stiffness to a desired level for removal and/or insertion.

To reduce the stiffness of the distal most region of endoscope 10 while maintaining the stiffness of a region ahead of the distal most end (that is, towards the proximal end), the inflatable balloon 40 may be pulled out of the distal most end using the links coupled to the inflatable balloon 40. In some embodiments, inflatable balloon 40 may be pulled out at about the same rate as endoscope 10 is pushed into the body cavity to keep the region of the endoscope 10 in the unconstricted body cavity flexible. In an embodiment of inflatable balloon in the form of a segmented balloon (FIG. 3C), balloon segments proximate the distal most end may be deflated while balloon segments proximal to the distal most end inflated to move the region of increased stiffness towards the proximal end 20 of endoscope 10 as the endoscope is inserted into the body cavity.

As indicated earlier, although the invention of the current disclosure is illustrated and described as being applied to an endoscope, the invention may be broadly applied to any transluminal device. It will be apparent to those skilled in the art that various modifications and variations can be made in the disclosed systems and processes without departing from the scope of the invention. Other embodiments of the invention will be apparent to those skilled in the art from consideration of the specification and practice of the invention disclosed herein. It is intended that the specification and examples be considered as exemplary only, with a true scope of the invention being indicated by the following claims.

We claim:

1. A method of using a transluminal device comprising:
   inserting a distal end of the device into a body cavity, the device including a lumen extending from a proximal end of the device to the distal end;
   positioning a balloon at a first location within the lumen, the first location being a location between the proximal end and the distal end; and
   moving the balloon from the first location to a second location in the lumen between the proximal end and the distal end; and
   inflating the balloon by admitting a fluid therein.

2. The method of claim 1, further including inserting the balloon into the lumen, and wherein the step of inflating the balloon is performed after positioning the balloon at the first location.

3. The method of claim 1, wherein the step of inflating the balloon is performed before positioning the balloon at the first location.

4. The method of claim 1, further including deflating the balloon by removing the fluid therefrom, and wherein deflating the balloon increases a flexibility of the device.

5. The method of claim 1, wherein inflating the balloon includes inflating a first section of the balloon independent of a second section of the balloon by admitting fluid into the first section while not admitting fluid into the second section, the first section and the second sections being different sections of the balloon, and wherein inflating the balloon decreases a flexibility of the device.

6. A method of using a medical device comprising:
   inserting an elongate section of the medical device into a body cavity, the elongate section having a distal end and a proximal end;
   positioning a balloon at a first location within the elongate section between the proximal end and the distal end; and
   adjusting a flexibility of the elongate section, wherein the flexibility of the elongate section is decreased when the balloon is inflated, and the flexibility is increased when the balloon is deflated.

7. The method of claim 6, further including axially moving the balloon between the proximal end and the distal end.

8. The method of claim 6, wherein the balloon extends substantially from the proximal end to the distal end of the elongate section.

9. The method of claim 6, wherein a length of the balloon is substantially smaller than a length of the elongate section.

10. A method of using a medical device comprising:
    inserting an elongate section of the medical device into a body cavity, the elongate section extending between a proximal end and a distal end of the device, and the elongate section including a first region and a second region between the proximal end and the distal end; and
    radially expanding a balloon within the elongate section to independently adjust the flexibility of each of the first region and the second region,
    wherein:
    the balloon is configured to radially expand from a deflated configuration to an inflated configuration by admitting a fluid therein, and
    the flexibility of the first region increases when the balloon is located in the first region and expands from the deflated configuration to the inflated configuration.

11. The method of claim 10, wherein a lumen extends within the elongate section from the proximal end to the distal end, and wherein the balloon is disposed within the lumen.

12. The method of claim 10, further comprising a step of moving, using a wire, the balloon from the first region to the second region.

13. The method of claim 10, wherein the balloon extends substantially from the proximal end to the distal end of the elongate section.

14. The method of claim 10, wherein a length of the balloon is substantially smaller than a length of the elongate section.

15. The method of claim 10, wherein the balloon includes multiple segments that are configured to inflate and deflate, wherein the multiple segments are separated by balloon sections that do not substantially inflate and deflate when the fluid is admitted into or removed from the balloon, and wherein some segments of the multiple segments are configured to inflate and deflate independently of other segments.

16. The method of claim 10, wherein the balloon is fixed in the device.

17. The method of claim 10, further including a lumen extending within the elongate section from the proximal end to the distal end, wherein the balloon is positioned within the lumen and configured to be axially movable between the proximal end and the distal end.

18. The method of claim 10, wherein the balloon extends substantially from the proximal end to the distal end of the elongate section.

19. The method of claim 10, wherein the balloon is fixed in the elongate section.

20. The method of claim 10, wherein the device includes a wire configured to move the balloon between a first region and a second region between the proximal end and the distal end.

* * * * *